United States Patent [19]

Schumacher et al.

[11] Patent Number: 5,780,221
[45] Date of Patent: Jul. 14, 1998

[54] IDENTIFICATION OF ENANTIOMERIC LIGANDS

[75] Inventors: Antonius Nicolass Maria Schumacher. Somerville; Peter S. Kim. Lexington. both of Mass.

[73] Assignee: Whitehead Institute for Biomedical Research. Cambridge. Mass.

[21] Appl. No.: 627,497

[22] Filed: Mar. 28, 1996

Related U.S. Application Data

[60] Provisional application No. 60/001,067, Jul. 11, 1995.

Related U.S. Application Data

[63] Continuation-in-part of Ser. No. 482,309, Jun. 7, 1995, abandoned, which is a continuation-in-part of Ser. No. 433,572, May 3, 1995.

[51] Int. Cl.$^6$ .............................. C12Q 1/70; C12Q 1/68; G01N 33/53
[52] U.S. Cl. .................... 435/5; 435/6; 435/7.1; 436/501; 436/518
[58] Field of Search ................ 435/5, 6, 7.1, 235.1; 436/501, 518

[56] References Cited

FOREIGN PATENT DOCUMENTS

93/25667  12/1993  WIPO .

OTHER PUBLICATIONS

Birnbaum et al., "Peptide Screening". Current Opinion in Biotechnology. vol. 3, pp. 49–54, 1992.

Ecker et al., "Rational screening of oligonucleotide combinatorial libraries for drug discovery." Nucleic Acids Research, vol. 21, No. 8, pp. 1853–1856, 1993.

Fisher, P.J., et al., "Calmodulin interacts with amphiphilic peptides composed of all D–amino acids", Nature, 368:651–653 (1994).

Jameson, B.J., et al., "A rationally designed CD4 analogue inhibits experimental allergic encephalomyelitis", Nature, 368:744–746 (1994).

Dooley, C.T., et al., "An all D–amino acid opioid peptide with central analgesic activity from a combinatorial library", Science, 266:2019–2021 (1994).

Lam, K.S., et al., "Discovery of D–amino acid–containing ligands with selectide technology", Gene, 137(1):13–16 (1993).

Dooley, C.T., et al., "New, potent, N–acetylated all D–amino acid opioid peptides", Peptides, Chemistry, Structure and Biology, Proceedings of the 13th Amer. Peptide Symposium, Jun. 20–25, 1993 Edmonton, Alberta, Canada.

Lam, K.S., et al., "Streptavidin–peptide interaction as a model system for molecular recognition", Peptides, Chemistry, Structure and Biology, Proceedings of the 13th Amer. Peptide Symposium, Jun. 20–25, 1993 Edmonton, Alberta, Canada.

Alexandropoulos, K., et al., "Proline–rich sequences that bind to SRC homology 3 domains with individual specificity", PNAS, USA, 92(8):3110–3114 (1995).

Gout, I., et ak., "The GTPase dynamin binds to and is activated by a subset of SH3 domains", Cell, 75(1):25–36 (1993).

Yu, H., et al., "Structural basis for the binding of proline–rich peptides to SH3 domains", Cell, 76(5):933–945 (1994).

Schumacher, T.N.M., et al., "Identification of D–peptide ligands through mirror–image phage display". Science, 271:1854–1856 (1996).

(List continued on next page.)

Primary Examiner—Lora M. Green
Attorney, Agent, or Firm—Hamilton, Brook, Smith & Reynolds, P.C.

[57] ABSTRACT

A method of identifying macromolecules (peptides, oligonucleotides, sugars and macromolecular complexes, such as RNA-protein complexes, protein-lipid complexes), which are not of the natural handedness (not of the chirality as they occur in nature or as a wild type molecule) and which are ligands for other chiral macromolecules.

14 Claims, 1 Drawing Sheet

OTHER PUBLICATIONS

Robson, B., "Dextroceutical™ Technology: New Pharmaceutical Opportunities Through the Looking Glass", *Development of Small Molecule Mimetic Drugs*, Washington Court Hotel, Washington, D.C., May 2–3, 1996.

Zawadzke L.E. and Berg, J.M., "A Racemic Protein", *J. Am. Chem. Soc.*, 114:4002–4003 (1992).

Cheadler, C., et al., "Identification of a Src SH3 Domain Binding Motif by Screening a Random Phage Display Library", *J. of Biol. Chem.*, 269(89):24034–24039 (1994).

Sparks, A.B., et al., "Identification and Characterization of Src SH3 Ligands from Phage–displayed Random Peptide Libraries", *J. of Biol. Chem.*, 269(39):23853–23856 (1994).

Rickles, R.J., et al., "Identification of Src, Fyn, Lyn, PI3K and Abl SH3 domain ligands using phage display libraries", *EMBO J.*, 13(23):5598–5604 (1994).

Milton, R.C. deL., et al., "Total Chemical Synthesis of a D–Enzyme: The Enantiomers of HIV–1 Protease Show Demonstration of Reciprocal Chiral Substrate Specificity", *Science*, 256:1445–1488 (1992).

Petsko, G. A., "On the Other Hand . . . ", *Science*, 256:1403–1404 (1992).

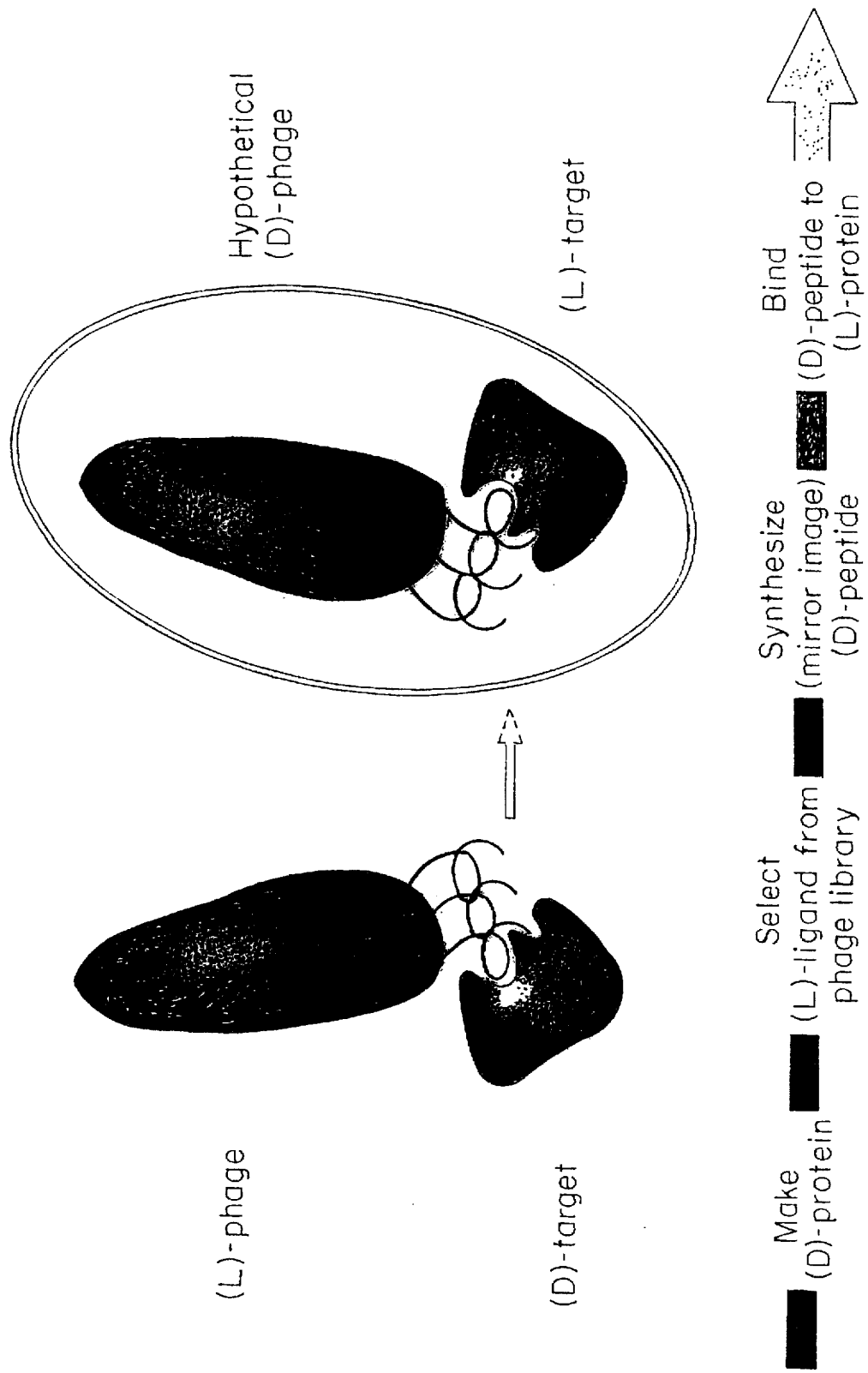

5,780,221

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 60 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Gly  Gly  Val  Thr  Thr  Phe  Val  Ala  Leu  Tyr  Asp  Tyr  Glu  Ser  Arg  Thr
 1                  5                           10                          15
```

```
Glu  Thr  Asp  Leu  Ser  Phe  Lys  Lys  Gly  Glu  Arg  Leu  Gln  Ile  Val  Asn
               20                  25                            30

Asn  Thr  Glu  Gly  Asp  Trp  Trp  Leu  Ala  His  Ser  Leu  Thr  Thr  Gly  Gln
          35                       40                       45

Thr  Gly  Tyr  Ile  Pro  Ser  Asn  Tyr  Val  Ala  Pro  Ser
     50                       55                      60
```

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Tyr  Gly  Gly  Arg  Glu  Leu  Pro  Pro  Leu  Pro  Arg  Phe
1                   5                        10
```

( 2 ) INFORMATION FOR SEQ ID NO:3:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 5
        ( D ) OTHER INFORMATION: /product="OTHER"
            / note= "The Ser at this location can be either Ser or Cys ( i x ) FEATURE:
        ( A ) NAME/KEY: Modified-site
        ( B ) LOCATION: 16
        ( D ) OTHER INFORMATION: /product="OTHER"
            / note= "Ser at this location can be either Ser or Cys."

( x i ) SEQUENCE DESCRIPTION: SEQ ID NO:3:

```
Ala  Asp  Gly  Ala  Ser  Xaa  Xaa  Xaa  Xaa  Xaa  Xaa  Xaa  Xaa  Xaa  Xaa  Ser
1                   5                        10                            15

Gly  Ala  Gly  Ala
               20
```

( 2 ) INFORMATION FOR SEQ ID NO:4:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA (other)

( x i ) SEQUENCE DESCRIPTION: SEQ ID NO:4:

```
CTATTCTCAC  TCGGCCGACG  GGGCTTSCNN  SNNSNNSNNS  NNSNNSNNSN  NSNNSNNSTS        60

CGCCGCTGGG  GCCGAAACTG  TTGAA                                                 85
```

( 2 ) INFORMATION FOR SEQ ID NO:5:

( i ) SEQUENCE CHARACTERISTICS:
        ( A ) LENGTH: 14 amino acids
        ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:5:

Ala Ser Trp Arg Tyr Asn Tyr Ala Phe Met Arg Tyr Ser Ala
1               5                   10

(2) INFORMATION FOR SEQ ID NO:6:

(i) SEQUENCE CHARACTERISTICS:
    (A) LENGTH: 14 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:6:

Ala Ser Met Trp Met Tyr Pro Tyr Pro Trp Gly Val Ser Ala
1               5                   10

(2) INFORMATION FOR SEQ ID NO:7:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:7:

Leu Pro Glu Val Pro Pro Leu Val Ala Pro
1               5                   10

(2) INFORMATION FOR SEQ ID NO:8:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:8:

Leu Ala Arg Ser Arg Leu Pro Ala Ile Pro
1               5                   10

(2) INFORMATION FOR SEQ ID NO:9:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:9:

Arg Met Ser Pro Leu Val Pro Leu Arg Asn
1               5                   10

(2) INFORMATION FOR SEQ ID NO:10:

(i) SEQUENCE CHARACTERISTICS:
    (A) LENGTH: 12 amino acids
    (B) TYPE: amino acid (C) STRANDEDNESS: single
(D) TOPOLOGY: linear (ii) MOLECULE TYPE: peptide (xi) SEQUENCE DESCRIPTION: SEQ ID NO:10:

```
Cys Leu Ala Arg Ser Arg Leu Pro Ala Ile Pro Ser
 1               5                  10
```

(2) INFORMATION FOR SEQ ID NO:11:

(i) SEQUENCE CHARACTERISTICS:
  (A) LENGTH: 14 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:11:

```
Arg Cys Leu Ser Gly Leu Arg Leu Gly Leu Val Pro Cys Ala
 1               5                  10
```

(2) INFORMATION FOR SEQ ID NO:12:

(i) SEQUENCE CHARACTERISTICS:
  (A) LENGTH: 14 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:12:

```
Ala Cys Lys Arg Phe Val Trp Arg Gly Gln Ala Leu Cys Ala
 1               5                  10
```

(2) INFORMATION FOR SEQ ID NO:13:

(i) SEQUENCE CHARACTERISTICS:
  (A) LENGTH: 12 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:13:

```
Cys Lys Arg Phe Val Trp Arg Gly Gln Ala Leu Cys
 1               5                  10
```

(2) INFORMATION FOR SEQ ID NO:14:

(i) SEQUENCE CHARACTERISTICS:
  (A) LENGTH: 12 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:14:

```
Cys Ser Arg Ala Ser Trp Arg Gly Leu Leu Phe Cys
 1               5                  10
```

(2) INFORMATION FOR SEQ ID NO:15:

(i) SEQUENCE CHARACTERISTICS:
  (A) LENGTH: 12 amino acids
  (B) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:15:

```
Cys Trp Tyr Leu Gly Tyr Trp Pro Gly Gln Glu Cys
1               5                   10
```

( 2 ) INFORMATION FOR SEQ ID NO:16:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Cys Leu Ser Gly Leu Arg Leu Gly Leu Val Pro Cys
1               5                   10
```

( 2 ) INFORMATION FOR SEQ ID NO:17:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Cys Leu Met Gly Leu Arg Leu Gly Leu Leu Pro Cys
1               5                   10
```

( 2 ) INFORMATION FOR SEQ ID NO:18:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

```
Cys Ala Tyr Gly Phe Lys Leu Gly Leu Ile Lys Cys
1               5                   10
```

( 2 ) INFORMATION FOR SEQ ID NO:19:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

```
Cys Lys Arg Phe Trp Arg Gly Gln Ala Leu Cys
1               5                   10
```

( 2 ) INFORMATION FOR SEQ ID NO:20:

( i ) SEQUENCE CHARACTERISTICS:
        ( A ) LENGTH: 12 amino acids
        ( B ) TYPE: amino acid ( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /product="OTHER"
/ note= "The amino acid at this location can also be Cys."

( i x ) FEATURE:
( A ) NAME/KEY: Modified-site
( B ) LOCATION: 12
( D ) OTHER INFORMATION: /product="OTHER"
/ note= "The amino acid at this location can also be Cys."

( x i ) SEQUENCE DESCRIPTION: SEQ ID NO:20:

Ser Xaa Xaa Xaa Xaa Xaa Xaa Xaa Xaa Xaa Xaa Ser
1               5                       10

( 2 ) INFORMATION FOR SEQ ID NO:21:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:21:

Ser Arg Met Ser Pro Leu Val Pro Leu Arg Asn Ser
1               5                       10

( 2 ) INFORMATION FOR SEQ ID NO:22:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:22:

Tyr Arg Cys Leu Ser Gly Leu Arg Leu Gly Leu Val Pro Cys Ala
1               5                       10                      15

( 2 ) INFORMATION FOR SEQ ID NO:23:

( i ) SEQUENCE CHARACTERISTICS:
( A ) LENGTH: 96 base pairs
( B ) TYPE: nucleic acid
( C ) STRANDEDNESS: single
( D ) TOPOLOGY: linear ( i i ) MOLECULE TYPE: DNA (other)

( x i ) SEQUENCE DESCRIPTION: SEQ ID NO:23:

TCTAACGTGA ATGATAGACG GCGAATCCCC AATGCGAAGC AGTGGTTTTG CAGTCGAGTT      60

GCTGTGTGCC GATGAGCGTT AACTTATTCG ACCAAA      96

( 2 ) INFORMATION FOR SEQ ID NO:24:

( i ) SEQUENCE CHARACTERISTICS:
( A ) LENGTH: 96 base pairs
( B ) TYPE: nucleic acid
( C ) STRANDEDNESS: single
( D ) TOPOLOGY: linear ( i i ) MOLECULE TYPE: DNA (other)

( x i ) SEQUENCE DESCRIPTION: SEQ ID NO:24:

```
TCTAACGTGA ATGATAGACG TTACGTGTCT ACACTATGTC GAGTTGCTGT GTGCCGATGA    60

ACGTGGGATT AGAGCGTGTT AACTTATTCG ACCAAA                              96
```

( 2 ) INFORMATION FOR SEQ ID NO:25:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: DNA (other)

( x i ) SEQUENCE DESCRIPTION: SEQ ID NO:25:

```
TCTAACGTGA ATGATAGACG TTACGTGTCT ACACTATGTC GAGTTGCTGT GTGCCGATGA    60

ACGTGGGAT                                                            69
```

1

IDENTIFICATION OF ENANTIOMERIC LIGANDS

RELATED APPLICATIONS

This application is a continuation-in-part of U.S. Provisional application number 60/001,067, filed Jul. 11, 1995, and is a continuation-in-part of U.S. Ser. No. 08/482,309, filed Jun. 7, 1995, now abandoned which is a continuation-in-part of U.S. Ser. No. 08/433,572, filed May 3, 1995, the teachings of which are incorporated herein by reference.

FUNDING

Work described herein was funded by the Howard Hughes Medical Institute/Life Sciences Research Foundation.

BACKGROUND

Genetically encoded libraries of peptides and oligonucleotides are well suited for the identification of ligands for many macromolecules. However, a major drawback of biologically encoded libraries is that the resultant ligands are subject to degradation by naturally occurring enzymes. Furthermore, because of their sensitivity to cellular proteases, peptides composed of naturally occurring L-amino acids are efficiently processed for major histocompatibility complex class II-restricted presentation to T helper cells ($T_H$ cells). As a result, L-peptides can induce a vigorous humoral immune response that impairs the activity of such drugs (Gill, T. J., et al., *Nature*, 197:746 (1963); Mauer, J., *J. Exp. Med.*, 121:339 (1965); Borek, F., et al., *Biochem. J.*, 96:577 (1965); Janeway, C. A. and Sela, M., *Immunol.*, 13:29 (1967); Dintzis, H. M., et al., *Proteins*, 16:306 (1993)).

The enantiomers of macromolecules of natural handedness make better drugs than the macromolecules of natural handedness. In contrast to naturally occurring L-peptide sequences and D-nucleic acid sequences, the enantiomers of these naturally occurring macromolecules (e.g., D-peptides and L-nucleic acids) are not good substrates for naturally occurring proteases and nucleases. In addition, the enantiomers of naturally occurring molecules do not elicit an efficient immune response.

Availability of D-peptides and L-nucleic acids for use as drugs is desirable.

SUMMARY OF THE INVENTION

The present invention is a method of identifying enantiomeric macromolecules (proteins, peptides, oligonucleotides, nucleic acids, sugars and macromolecular complexes, such as RNA-protein complexes and protein-lipid complexes), which are not of the natural handedness (not of the chirality as they occur in nature or as a wild type molecule) and which are ligands for other chiral macromolecules, which are referred to as target or desired macromolecules. Target or desired macromolecules include proteins (e.g., polypeptides and peptides), such as hormones, enzymes, antibodies, antigens, oligonucleotides (DNA, RNA). In one embodiment, the present invention is a method of identifying D-amino acid peptide ligands which bind a target or desired L amino acid peptide. In a second embodiment, this invention is a method of identifying peptides comprised of D-amino acid residues that are ligands for oligonucleotides (RNA or DNA). In a further embodiment, the present invention is a method of identifying RNA or DNA oligonucleotides which are of the opposite chirality from that which occurs in nature. DNA occurs in nature as a D isomer.

2

In one embodiment, the present invention relates to a method of producing a macromolecule of non-natural handedness that binds to a target macromolecule of natural handedness (e.g., peptide, oligonucleotide), which is performed as follows: an enantiomer of the target macromolecule or of a domain characteristic of the target molecule is provided and contacted with a library of macromolecules of natural handedness, under conditions appropriate for binding of a macromolecule of natural handedness in the library with the enantiomer; as a result, the enantiomer binds a macromolecule of natural handedness present in the library. The enantiomer of the macromolecule of natural handedness which is bound to the enantiomer of the target macromolecule is produced; the enantiomer of the macromolecule of natural handedness is a macromolecule of non-natural handedness which binds to the target macromolecule of natural handedness. That is, the enantiomer of a macromolecule which is present in the library and binds to the enantiomer of the target molecule is produced; the result is a macromolecule of non-natural handedness which binds the target molecule (of natural handedness).

In another embodiment, the present invention relates to a method of producing a macromolecule of non-natural handedness that binds to a target macromolecule of natural handedness, which is performed as follows: an enantiomer of the target macromolecule or of a domain characteristic of the target molecule is provided and contacted with a library of macromolecules of natural handedness, under conditions appropriate for binding of a macromolecule of natural handedness in the library with the enantiomer; as a result, the enantiomer binds a macromolecule of natural handedness present in the library. A macromolecule of natural handedness which is bound to the enantiomer is identified and sequenced. The enantiomer of the macromolecule of non-natural handedness, which is bound to the enantiomer of the macromolecule of natural handedness or of a characteristic domain thereof, is produced; the resulting enantiomer of the macromolecule of natural handedness is a macromolecule of non-natural handedness which binds to the target macromolecule of natural handedness.

In another embodiment, the present invention relates to a method of producing a D amino acid peptide that binds to a target L macromolecule. The method is performed as follows: a D amino acid peptide of the target L macromolecule or of a domain characteristic thereof and a library of L amino acid peptides are provided. The library and the D amino acid peptide of the target macromolecule are contacted under conditions appropriate for binding of an L amino acid peptide in the library with the D amino acid peptide; as a result, the D amino acid peptide binds an L amino acid peptide present in the library. An L amino acid peptide present in the library which is bound to the D amino acid peptide is identified and sequenced. A D amino acid peptide of the L amino acid peptide identified in the library or of a characteristic domain thereof is produced; the resulting D amino acid peptide binds to the target L macromolecule.

In another embodiment, the present invention relates to a method of producing an L oligonucleotide that binds to a target L macromolecule. The method is performed as follows: a D amino acid peptide of the target L macromolecule or of a domain characteristic thereof and a library of D oligonucleotides are provided. The library is contacted with the D amino acid peptide under conditions appropriate for binding of a D oligonucleotides in the library with the D amino acid peptide, whereby the peptide binds a D oligonucleotides present in the library. A D oligonucleotide which is bound to the D amino acid peptide is identified and sequenced. An L oligonucleotide of the D oligonucleotide identified in the library or of a characteristic domain thereof, is produced; the L oligonucleotide binds to the target L macromolecule.

In a further embodiment of the present invention, an L amino acid peptide which binds a D amino acid peptide of interest is identified as follows: a phage display library which comprises L amino acid peptides displayed on phage surfaces is provided and contacted with the D amino acid peptide of interest, under conditions appropriate for binding of L amino acid peptides displayed on phage surfaces with the D amino acid peptide of interest. Phage which have on their surfaces the D amino acid peptide of interest, bound to an L amino acid peptide displayed on the surface (i.e., which have on their surfaces a D amino acid peptide-displayed L amino acid peptide complex) are identified. The displayed L amino acid peptide in the complex is an L amino acid peptide which binds the D amino acid of interest.

Optionally, the amino acid sequence of the L amino acid peptide displayed on the surface of the phage can be determined and the D amino acid peptide which corresponds to the amino acid sequence of the L amino acid peptide can be synthesized, resulting in production of a D amino acid peptide which corresponds to the L amino acid peptide displayed on the phage surface. In one embodiment, described herein, L amino acid peptides displayed on phage surfaces bind D amino acid peptides of the SRC homology 3 domain (SH3 domain). A further embodiment is a method of making a D amino acid protein which corresponds to a target L amino acid protein, which can be any protein (including polypeptides, peptides) for which a binding peptide is desired. In this embodiment, a phage display library which comprises a mixture of proteins displayed on phage surfaces is contacted with a D amino acid peptide corresponding to the target L amino acid protein or corresponding to a domain characteristic of the target L amino acid protein, under conditions appropriate for binding of L amino acid peptides displayed on phage surfaces with D amino acid proteins. The mixture comprises the target L amino acid protein or a characteristic L amino acid peptide domain thereof. Phage which have on their surfaces the D amino acid peptide bound to an L amino acid peptide displayed on the surface are identified. The amino acid sequences of the L amino acid peptides displayed on the surfaces of phages identified are determined and a D amino acid protein which corresponds to an amino acid sequence of an L amino acid peptide is synthesized, resulting in production of a D amino acid peptide which corresponds to the target L amino acid protein.

The present invention also relates to a method of obtaining an L nucleic acid which binds an L amino acid peptide of interest. In this method, a collection of D nucleic acid sequences (e.g., a DNA library) is provided and contacted with a D amino acid peptide of interest, under conditions appropriate for binding of the D nucleic acid with the D amino acid peptide of interest. A D nucleic acid which binds to the D amino acid peptide is isolated and the nucleotide sequence of the D nucleic acid is determined. The D nucleic acid sequence which binds to the D amino acid peptide of interest is prepared using L nucleotides, resulting in the production of an L nucleic acid sequence which binds an L amino acid peptide. A further embodiment of the invention relates to a method of obtaining an L nucleic acid sequence which binds a D nucleic acid which comprises providing a collection of D nucleic acid sequences and contacting the D nucleic acid sequences with an L nucleic acid sequence. A D nucleic acid sequence which binds to the L nucleic acid sequence, thereby producing a D nucleic acid sequence—L nucleic acid sequence complex, is identified. The nucleotide sequence of the D nucleic acid sequence which binds to the L nucleic acid sequence is determined. The D nucleic acid sequence is synthesized using L nucleotides, resulting in the production of an L nucleic acid sequence which binds a D nucleic acid.

Also the subject of the present invention are synthetic D amino acid peptides, such as D amino acid peptides identified and produced by the methods described herein, including but not limited to synthetic amino acid peptides which bind the SH3 domain, synthetic D amino acid peptides corresponding to all or a portion of the SH3 domain and, more generally, synthetic D amino acid peptides which bind a domain of an intracellular signaling protein. In addition, oligonucleotides (RNA, DNA) of non-natural handedness, such as oligonucleotides identified and produced by the methods described herein are the subject of this invention.

D amino acid peptides and L nucleic acid sequences of the present invention are useful as drugs. For example, D amino acid peptides are not good substrates for naturallyoccurring proteases (i.e., resistant to proteolytic degradation) and do not elicit an immune response comparable to that elicited by L amino acid peptides.

BRIEF DESCRIPTION OF THE FIGURES

FIG. 1 is a graphic representation of the identification of a D-peptide ligand through mirror-image phage display.

DETAILED DESCRIPTION OF THE INVENTION

The synthetic enantiomer of a structured biopolymer folds into the mirror-image conformation of the natural molecule; likewise, for a bimolecular complex, the two enantiomers of the original partner molecules also form a complex, with mirror-image symmetry to the original. The present invention is based on the discovery that identification of a macromolecule of natural handedness (e.g., D-peptide, L-single-stranded oligonucleotide) that binds the enantiomer of a chiral biological target molecule, provides for a method of identifying a macromolecule of non natural handedness which binds the natural form of the target. Such enantiomeric macromolecules, which are not susceptible to proteases, are then screened for their ability to interfere with the biological activity of the target. Thus, the present invention constitutes an attractive approach to the development of new long-acting therapeutic or diagnostic molecules.

The present invention relates to a method of identifying enantiomeric macromolecules, including peptides, polypeptides, proteins, oligonucleotides and sugars, as well as macromolecular complexes (oligonucleotide-protein complexes, protein-lipid complexes), which are not of the naturally-occurring or wildtype handedness (i.e., chirality) and which are ligands for other chiral molecules (peptides, oligonucleotides and macromolecular complexes). In the method of the present invention, an enantiomer of a naturally occurring target macromolecule is prepared and used to isolate from a collection of naturally occurring macromolecules, a naturally occurring ligand that interacts with the enantiomer. Consequently, the enantiomeric form of the isolated naturally occurring ligand will interact with the naturally-occurring target macromolecule.

The target macromolecule of natural handedness can be any macromolecule having one or more chiral centers. The target macromolecule (chiral targets) include, but are not limited to, nucleic acids (DNA, RNA), proteins or a characteristic domain thereof (e.g., peptide), peptides, polypeptides, oligonucleotides, carbohydrates, sugars, oligonucleotide-protein complexes (RNA-protein complex) and protein-lipid complexes, all of which contain chiral centers. Examples of target macromolecules which are proteins (polypeptides, peptides) include a domain of an intracellular signaling protein (e.g., the SH3 domain), vasopressin, Factor IX GLA domain, tissue factor fibronectin type III modules, interleukin-8 (Clore, G. M., et al., *Biochemistry*, 29:1689–1696 (1990)), Thrombomodulin EGF-like domain (Lentz, S. R., et al., *J. of Biological Chem.*, 288(20):15312–15317 (1993)), GPII$_b$-III$_a$ cytoplasmic domain (Muir, T. W., et al., *Biochemistry*, 33:7701–7708 (1994)), Factor VIIa GLA domain, Factor IX EGF-like domain (Yang, Y., *Protein Science*, 3:1267–1275 (1994)), human immunodeficiency virus (HIV) protease, NH$_2$-terminal SH3 domain GRB2, (Wittekind, M., et al., *Biochemistry*, 33:13531–13539 (1994)), COOH-terminal SH3 domain GRB2 (Kohda, D., et al., *Structure*, 2:1029–1040 (1994), P120$^{GAP}$ SH3 domain (Yang, Y. S., et al., *The EMBO Journal*, 13(6):1270–1279 (1984)), Vascular permeability factor/vascular endothelial growth factor. Examples of target macromolecules which are oligonucleotides (RNA, DNA) include HIV RRE (rev responsive element), HIV Tar, BCR-AB1 fusion DNA sequences.

In the method of the present invention, an enantiomer of a naturally occurring macromolecule (e.g., the enantiomer of the target macromolecule or the enantiomer of the macromolecule of natural handedness identified in the library) is prepared using routine methods. The enantiomer of the naturally occurring macromolecules (i.e., a macromolecule of non-natural handedness) can be prepared through the use of components of the opposite handedness from that which occurs in nature (e.g., the use of D amino acids for synthesis of mirror image peptides or the use of L-nucleic acids for synthesis of mirror image oligonucleotides). For example, a D-peptide for use in the present invention can be synthesized chemically and purified using affinity chromatography as described in Example 1. Other methods for preparing the enantiomers of naturally occurring macromolecules are known in the art.

Identification and production of the macromolecules of non-natural handedness which bind to the target macromolecule can be carried out using any collection of macromolecules of natural handedness. The method described is applicable to all situations in which a biologically encoded library is used to isolate structures that interact with a chiral target (or chiral "bait") (Scott, J. K. and Smith, G. P., *Science* 249:386 (1990); Devlin, J. J., et al., *Ibid.* 249:404 (1990); Cwirla, S. E., et al., *Proc. Natl. Acad. Sci. USA* 87:6378 (1990); Cull, M. G., et al., *Proc. Natl. Acad. Sci. USA* 89:1865 (1992); Mattheak, L. C., et al., *Proc. Natl. Acad. Sci., USA* 91:9022 (1994). As described in the exemplification, a biologically encoded library, such as a phage display library (mirror image phage display) can be used in the methods of the present invention. Because ribonucleotide and deoxyribonucleotides also contain chiral centers which are recognized by nucleases, this approach equally applies to both RNA libraries and DNA libraries (Bock, L. C., et al., *Nature*, 355:564 (1992)). Therefore, the type of libraries for which this approach is useful include both RNA (e.g. SELEX), DNA (e.g.,DNA library) and peptide libraries (e.g., in vitro transcription/translation based libraries mono-and poly-valent phage libraries and 'peptide on plasmid' libraries). Use of a DNA library in the method of the present invention is described in Example 5. Examination of the vast amount of structural space represented in these libraries can yield new ligands for proteins of biological and medical importance. Phages which specifically interact with the D-enantiomer and the L-enantiomer of a of a naturally-occurring (wildtype) macromolecule have been isolated, as described in the exemplification.

The selection process of the macromolecule of natural handedness in the library bound to the enantiomer of the target macromolecule can be performed in an achiral solvent (e.g., water), and the interaction between the naturally occurring macromolecule and the enantiomer is unlikely to require any chiral cofactors. An example of a selection process that can be used is described in the exemplification. Modification of the selection process can be performed using skills known in the art.

In a particular embodiment, D amino acid peptides which are ligands for a naturally-occurring L amino acid peptide (which includes polypeptides and proteins) are identified by the claimed method. Such D amino acid peptides can be produced to correspond precisely to the L amino acid peptide (except the constituent amino acids are D, not L enantiomers) or can be modified, such as by a substitution, deletion or modification of one or more constituent amino acids.

In another embodiment, L nucleic acid sequences which bind to D nucleic acid sequences or L amino acid peptides are identified by the claimed methods. The L nucleic acid sequences can be produced to correspond to the D nucleic acid (except the constituent nucleotides are L nucleotides) or can be modified, such as by substitution, deletion or modification of one or more of the constituent L nucleotides.

Synthetic and biologically encoded libraries have proven to be extremely useful for the identification of ligands and nucleic acid sequences for a large variety of macromolecules. Synthetic peptide libraries composed of (D)-amino acids have been favored over gene-based techniques such as phage display Scott, J. K. and Smith, G. P., *Science* 249:386 (1990); Devlin, J. J., et al., *Ibid.* 249:404 (1990); Cwirla, S. E., et al., *Proc. Natl. Acad. Sci. USA* 87:6378 (1990), 'peptide on plasmid' Cull, M. G., et al., *Proc. Natl. Acad. Sci. USA* 89:1865 (1992) and in vitro translation based systems Mattheak, L. C., et al., *Proc. Natl. Acad. Sci., USA* 91:9022 (1994) because the resulting peptides are insensitive to proteolytic digestion and fail to induce an efficient immune response. Furthermore, peptides composed of (D)-amino acids can be absorbed intestinally (Pappenheimer, J. R., et al., *Proc. Natl. Acad. Sci. USA* 91:1942 (1994)). Cyclosporin A, an 11 residue cyclic peptide composed mainly of (D)-amino acids, is a leading immunosuppressant and is generally given orally (Ptachcins, R. J., et al., *Clin. Pharmacokinetics*, 11:107 (1986)).

Although the screening of a (D)-amino acid library has recently led to the identification of a peptide with analgesic activity Dooley, C. T., et al., *Science* 266:2019 (1994), the proportion of sequence space that can be sampled in synthetic libraries is generally only a fraction of what can be attained through the use of biologically encoded systems. Because of this lower degeneracy, and more importantly, because of the lack of intermediate amplification steps, the use of synthetic libraries has not always been as successful as the use of phage display libraries in the identification of ligands.

Proteins composed of (D)-amino acids have a chiral specificity for substrates and inhibitors that is the exact opposite of that of the naturally occurring (L)-amino acid protein Del Milton, R. C., et al., *Science*, 257:1445 (1992); Petsko, G. A., *Ibid*, 256:1403 (1992); Zawadzke, L. E. and Berg, J. M., *J. Am. Chem. Soc.*, 114:4002 (1992). Although in certain instances (D)-amino acid ligands can be obtained by either making the (D)-enantiomer of a natural ligand (Fisher, P. J., et al., *Nature* 368:651 (1994)), or by making the 'reverse' (D)-enantiomer (Jameson, B. A., et al., *Nature* 368:744 (1994)), such methods have no general applicability (Brady, L. and Dodson, G., *Nature* 368:692 (1994)).

A more general method to obtain (D)-amino acid ligands could be the selection of peptides from a biologically encoded library using the (D)-enantiomer of a protein of interest. Because the (D)- and (L)-protein have a chiral specificity for substrates and inhibitors that is the exact opposite, the (D)-enantiomeric form of the phage-displayed peptides that interact with the (D)-protein will interact with the protein of the natural handedness.

The validity of this approach has been shown by the isolation of phage that specifically interact with the Denantiomer of the SRC homology 3 domain (SH3 domain). As described in Example 1, to examine the possible use of the mirror image relationship between (L)- and (D)-proteins for the identification of (D)-amino acid ligands from phage libraries, a (D)-amino acid version of the SH3 domain of the c-Src tyrosine kinase was synthesized. SH3 domains are 55–70 amino acid protein domains that are found in a variety of intracellular effector molecules (reviewed in Schlessinger, J., *Curr. Opin. Genet. Dev.*, 4:25 (1994)). Because c-SRC activity is essential for osteoclast-mediated bone resorption, interference with SRC function may be of value in the treatment of osteoporosis (Soriano, P. et al., *Cell*, 64:693 (1992); Lowe, C., *Proc. Natl. Acad. Sci USA*, 90:4485 (1993); Seymour, J. F., *Science and Medicine*, 2:48 (1995). SH3 domains interact with sequence elements in their cellular targets that form type II poly-proline helices of 8 to 10 residues (Rickles, R. J., et al., *EMBO J.*, 13:5598 (1994); Sparks, A. B., *J. Biol. Chem.*, 269:23853 (1994); Cheadle, C., et al., *Ibid*, 269:24034 (1994); Yu, H., et al., *Cell*, 76:933 (1994); Feng, S., et al., *Science* 266:1241 (1994); Lim, W. A., et al., *Nature*, 372:375 (1994). Mediating protein interactions in intracellular cell signalling proteins, and interference with the signalling of SH3 domain containing proteins would be desirable. Although ligands or substrates for a variety of SH3 domains have been isolated from phage display libraries (Rickles, R. J., et al., *EMBO J.*, 13:5598 (1994); Sparks, A. B., *J. Biol. Chem.*, 269:23853 (1994); Cheadle, C., et al., *Ibid*, 39:24034 (1994)), the identification of such sequences from a synthetic (L)-amino acid peptide library was possible only with prior knowledge of the sequences of the preferred ligands (Yu, H., et al., *Cell*, 76:933 (1994)). Thus, the identification of (D)-amino acid ligands for SH3 domains from synthetic libraries is unlikely to be successful, in the absence of prior sequence or structure information about potential ligands.

The L- and D-enantiomers of the chicken c-SRC domain were prepared by bacterial expression and chemical synthesis, respectively. The biotinylated, synthetic, 60-amino acid D-SH3 domain was refolded and purified by affinity chromatography, with a D-amino acid version of a known peptide ligand for the SH3 domain (Yu, H., et al., *Cell*, 76:933 (1994)). As expected, bacterially expressed L-SH3 was retained on an affinity column with the L-enantiomer of this peptide, but not with the D-enantiomer, which indicates that the interaction of the SH3 domain with its substrates is stereospecific.

A phage library was constructed in which random, 10-residue peptide sequences were expressed at the $NH_2$-terminus of the pIII protein of the bacteriophage fd (Scott, J. K. and Smith, G. P., *Science*, 249:386 (1990). Because many natural bioactive peptides, such as the immunosuppressant cyclosporin and the tumor promoter microcystin, are cyclic, the library was designed to include a large number of sequences that have a propensity for disulfide bond formation (Smith, G. P. and Scott, J. K., *Methods Enzymol.*, 217:228 (1993)). When the L-SH3 domain was used to screen this phage display library for interacting peptide sequences, disulfide-free polyproline-type sequences that have been identified by others were isolated (Yu, H., et al., *Cell*, 76:933 (1994); Rickles, R. J. et al., *EMBO J.*, 13:5598 (1994); Sparks, A. B., et al., *J. Biol. Chem.*, 269:23853 (1994); Cheadle, C., et al., *ibid.*, p. 24034)).

When the same phage display was screened with the D-SH3 domain, a series of peptide sequences that showed no obvious sequence similarity to the L-SH3-binding sequences was isolated and grouped in three classes (Table 1). These peptides all interact with the substrate binding site of the SH3 domain as they were eluted with the (D)-YGGRELPPLPRF peptide (SEQ ID NO: 2). These phage-displayed peptides that bind to the D-SH3 domain are characterized by a combination of conserved leucine and glycine residues and a conserved arginine or lysine residue. In contrast to the L-peptide ligands for the L-SH3 domain (Yu, H., et al., *Cell*, 76:933 (1994); Rickles, R. J. et al., *EMBO J.*, 13:5598 (1994; Sparks, A. B., et al., *J. Biol. Chem.*, 269:23853 (1994); Cheadle, C., et al., *ibid.*, p. 24034)), the positively charged residues in the ligands for the D-SH3 domain are located in the middle of a stretch of conserved residues, which suggests that the mode of ligand binding is different in the two forms. Furthermore, all ligands for the D-SH3 domain contain a pair of cysteine residues, a property that is not observed for the L-peptides that interact with the L-SH3 domain (Yu, H., et al., *Cell*, 76:933 (1994); Rickles, R. J. et al., *EMBO J.*, 13:5598 (1994; Sparks, A. B., et al., *J. Biol. Chem.*, 269:23853 (1994); Cheadle, C., et al., *ibid.*, p. 24034)). The disulfide bond may increase the affinity of these peptides for the D-SH3 domain by reducing the number of possible conformers.

Confirmation that the D-amino acid enantiomers of the peptides expressed by these phage particles interact with the all-L-amino acid SH3 domain is carried out using standard binding and detection methods. As described in Example 2, a D-peptide denoted Pep-D1, which is the mirror image of one of the phage-displayed peptides that bind to the D-SH3 domain, was synthesized and its interaction with the bacterially expressed L-SH3 domain examined. An indirect binding assay was used to verify that the (D)-SH3 domain binds to the substrate binding site of the (L)-SH3 domain.

As described in Example 3, heteronuclear magnetic resonance (NMR) experiments were performed on the $^{15}N$-labeled SH3 domain in the absence and presence of Pep-D1 to determine the binding site of this D-peptide in the SH3 domain. Residues in the SH3 domain that interact with Pep-D1 were identified through changes in amide $^1H$ or $^{15}N$ chemical shifts upon the addition of the D-peptide ligand.

In all cases the ligands that are isolated through this procedure are significantly less or not susceptible to the mechanisms that impair the activity of their biological counterparts. For example, the ligands isolated through the method described herein are significantly less or not susceptible to RNase and DNase activity for nucleotide-based ligands (Ashley, G. W., *J. Am. Chem. Soc.* 114:9731 (1992); Urata, H., et al., *J. Am. Chem. Soc.*, 113:8174 (1991) and proteolysis and activation of an immune response for peptide-based ligands (Gill, T. J., et al., *Nature* 197:746

(1963); Mauer, P. H., *J. Exp. Med.*, 121:339 (1965); Borek, F., et al., *Biochem., J.,* 96:577 (1965); Janeway, C. A. and Sela, M., *Immunology* 13:29 (1967); Ditzis, H. M., et al., *Proteins,* 16:306 (1993)).

The approach described here to isolate ligands that are not of the natural handedness is unique for the isolation of oligonucleotide-based ligands, as all the approaches used thus far lead only to the isolation of ligands of the natural handedness. Consequently, such 'conventional' ligands are susceptible to degradation by natural occurring enzymes. In contrast, the synthesis and screening of synthetic peptide libraries composed of D-amino acids is technically feasible. However, both because of the high number of compounds that can be screened in biologically encoded library systems (several orders of magnitude higher than can be achieved for synthetic peptide libraries) and the beneficial effects of the intermediate amplification steps used, such systems when combined with the technology described here yield superior results.

Specifically, synthetic peptide based strategies have an upper limit in degeneracy that is determined either by peptide solubility limits and detection limits for the assay used (for synthetic combinatorial libraries and other solution-based peptide libraries), or for solid phase based libraries, by volume considerations. Secondly, the intermediate amplification steps that are used in biologically encoded library systems allow the identification of ligands in situations where background binding is high (in systems that do not employ amplification steps a specific ligand will only be identified if it constitutes an easily detectable part of the total pool of recovered molecules after a single round of screening). Thirdly, phage display and other biologically encoded library systems allow for the maturation of affinities through mutation of the encoding DNA through processes such as error-prone PCR. Finally, phage libraries can accommodate inserts of significant length as compared to synthetic peptide based libraries. This not only allows the possible isolation of ligands of a different size class, but significantly increases the complexity of short ligands that are contained (as sliding windows) within these inserts.

As described in Example 4, identification of D-amino acid peptide ligands which interact with a specific target as described herein can be used to provide guidelines for the design of biased (D)-amino acid peptide and peptide-based libraries. The libraries can subsequently be used to isolate novel ligands.

The invention is further illustrated in the following examples, which are not intended to be limiting in any way.

EXAMPLE 1

Identification of Phage Which Sgecifically Interact With D-Amino Acid Peptides

Preparation of the L-SH3 domain

The residue numbering system is that of the full-length chicken c-SRC protein. Residues 81 to 140 of chicken c-SRC were cloned in other Hind III-Bam HI sites of the plasmid pMMHb (Staley, J. P. and Kim, P. S., *Protein Science,* 3:1822 (1994)). In this plasmid, proteins are expressed as a fusion with a modified form of the TrpLE leader sequence in which the methionine residues have been replaced with leucine and the cysteine residues have been replaced with alanine (Staley, J. P. and Kim, P. S., *Protein Science,* 3:1822 (1994)), and a stretch of nine histidine residues has been inserted into the COOH terminal region of the leader sequence. Expression of the fusion protein encoded by the plasmid pMMHb-SRC SH3 was induced at an absorbance of 0.6 at 600 nm by the addition of 0.4 mM isopropyl-β-D-thiogalactopyranoside (IPTG) (Research Organics) to *Escherichia-coli* BL21-(DE3) pLys S cells (Strategene). After induction for 2 hours, cells were centrifuged and inclusion bodies were isolated. Recombinant protein was purified by resuspension of inclusion bodies in 6 M guanidine-HCland, 0.2 M tris, pH 8.7 (buffer A) and chromatography on a $Ni^{2+}$ column ($Ni^{2+}$-NTA-agarose; Qiagen). After elution, dialysis against water, and lyophilization, the fusion protein was dissolved in 70% formic acid and cleaved with CNBr (Stanley, J. P. and Kim P. S., *Protein Science,* 3:1822 (1994)). Dialyzed and lyophilized material was subsequently taken up in buffer A, and purified by chromatography on a $Ni^{2+}$ column (after cleavage, the isolated SH3 domain flows through the column, whereas uncleaved fusion protein and the cleaved TrpLE leader sequence are retained). After dialysis (against PBS buffers of decreasing ionic strength, and finally against water) and lyophilization, the purity and identity of the SH3 domain were confirmed by high-performance liquid chromatography (HPLC) analysis at neutral pH and by laser desorption mass spectrometry (expected, 6686 daltons; observed, 6683 daltons).

Synthesis of the all D-Src SH3 domain

The all D amino acid SH3 domain, sequence GGVT-TFVALYDYESRTETDLSFKKGERL-QIVNNTEGDWWLAHSLTTGQTGYIPSNYVAP S-COOH-terminus (SEQ ID No: 1), residues 81–140 of chicken c-SRC, was synthesized on HMP resin (ABI/Perkin Elmer) with an ABI 431A peptide synthesizer and ABI fastmoc cycles (Fmoc chemistry with HBTU activation and capping with acetic anhydride). Protected D-amino acids were obtained from Bachem California., Bachem Bioscience, Advanced Chemtech, and Novabiochem. For D-Ile and D-Thr, the side chain enantiomers were used, in which the chirality of the side chain is also inverted relative to naturally occurring L-Thr and L-Ile. After completion of the synthesis, the $NH_2$-terminus of the peptide was modified with NHS-LC-biotin II (Pierce). After cleavage, the peptide was lyophilized, dissolved in 6 M guanidine HCl, pH 6.0, and dialyzed against 100 mM $NaHPO_4$ and 100 mM NaCl, pH 6.0, with the use of dialysis tubing with a molecular cutoff of 3,500 daltons (D) (Spectra/Por). After dialysis the material was spun briefly to remove insoluble debris, and the supernatant was subsequently dialyzed against 5% acetic acid and lyophilized. The peptide was dissolved at a concentration of 3.3 mg/ml in Tris-buffered saline (50 mM Tris, pH 7.5, and 150 mM NaCl) containing 1 mM biotin. The full biotinylated 60 amino acid (D)-SH3 domain length product was refolded and purified by affinity chromatography on an all-(D) version of a known substrate for the Src SH3 domain (D)-YGGRELPPLPRF (SEQ ID NO:2). Yu, H., et al., *Cell,* 76:933 (1994)), that was biotinylated and immobilized on a streptavidin-agarose column (Pierce). This peptide is a derivative of an all (L)-peptide shown to bind to the all (L)-SH3 domain (Yu, H., et al., *Cell.*76:933–945 (1994)), with an $NH_2$-terminal YGG added to facilitate concentration determination (H. Edelhoch, *Biochemistry,* 6:1948 (1967)). The L-peptide with the same $NH_2$-terminal YGG served as a control ligand in the experiments. As expected, bacterially expressed (L)-SH3 (residues 81–140 of chicken c-Src were expressed) can be retained on the (L)-enantiomer but not on the (D)-enantiomer of this peptide, indicating that the interaction of the SH3 domain with its substrates is stereospecific.

Chromatography fractions were analyzed by laser desorption mass spectrometry on a Voyager mass spectrometer (Perceptive Biosystems). Fractions containing material of the expected mass (expected, 7027 daltons; observed 7027 daltons to 7035 daltons) were pooled and dialyzed against water for 72 hrs, lyophilized and taken up in water at a concentration of 107 µg/ml.

Production of phage library

The phage library was designed to provide expression of random peptides as $NH_2$-terminal fusions with filamentous phage pIII protein. Typically, 3–5 copies were present per phage particle, to permit isolation of low/intermediate affinity ligands.

DNA encoding a 10-residue random insert with flanking serine or cysteine residues (S/C-$X_{10}$-S/C) (SEQ ID NO:20) was prepared by PCR of an 85 residue oligonucleotide (Smith, G., "Cloning in Fuse vectors", Division of Biological Sciences, University of Missouri (Edition of Feb. 10, 1992)) using biotinylated primers as described (Smith, G. P. and Scott, J. K., Methods Enzymol., 217:228 (1993)).

The insert design was: $NH_2$-A-D-G-A-S/C-$X_{10}$-S/C-G-A-G-A-PIII (SEQ ID NO:3).

85 Residue Oligonucleotide:
5'-C.TAT.TCT.CAC.TCG.GCC.GAC.GGG.GCT.TSC. (NNS)$_{10}$.TSC.GCC.GCT .GGG.GCC.GAA. ACT.GTT.GAA-3' ((SEQ ID NO: 4)

In which S=C/G N=A/T/C/G
(equimolar mixtures)

After purification of the PCR product and digestion with Bgl I, the end pieces were removed through the use of streptavidin-coated agarose beads (Pierce). The PCR product was subsequently ethanol precipitated and analyzed by electrophoresis on polyacrylamide gel.

The library was made by ligation of a random PCR product into Sfi I-cut Fuse 5 vector. After ligation the reaction mixture was extracted with phenol and chloroform, ethanol-precipitated and taken up in 10 mM Tris/1 m mM EDTA (pH 8.0). The ligation product was subsequently transferred into electrocompetent MC1061 cells (Biorad) using a Bio-Rad E. coli pulser and 0.1 cm cuvettes. After non-restrictive growth for 1 hr aliquots of transformed cells were plated on tetracycline-containing plates to determine the efficiency of transformation, yielding an initial library of $3.6 \times 10_8$ transformants. The transformation mixture was subsequently diluted to a volume of 400 ml LB and 20 µg/ml tetracycline, and grown for an additional 14 hrs. A phage stock was prepared by two successive polyethylene glycol (PEG) precipitations of the culture supernatant as described. The phage stock was finally resuspended in tris buffered saline/$NaN_3$ and titered by infection of K91-kan cells (A21), yielding a total of $2.8 \times 10^{11}$ transforming units. The randomness of the inserts was confirmed by sequencing of individual clones. $4 \times 10^{10}$ transforming units were subsequently used to infect K91-kan cells to generate an amplified library. After 18 hrs phage were purified by three repetitive PEG precipitations yielding 10 ml of the amplified phage library ($1.2–10^{12}$ transforming units/ml) in TBS/$NaN_3$. The quality of the library was confirmed by selection of phage that expressed inserts that interact with 1) the lectin concanavalin A (Con A) (Oldenburg, K. R. et al., Proc. Natl. Acad. Sci. USA, 89:5393 (1992); Scott, J. K. et al., ibid, p. 5398); 2) two mouse monoclonal antibodies raised against the mouse MHC class I heavy chain; and 3) a bacterially expressed form of the Src SH3 domain, all screens giving the expected results.

Con A screen
After 3 rounds
AS W R Y N Y A F M R Y SA (SEQ ID No: 5) (1)
AS M W M Y P Y P W G V SA (SEQ ID No: 6) (9)

Screening of the phage library

The phage display was screened with the D-SH3 domain and a series of peptide sequences, which showed no obvious sequence similarity to the L-SH3-binding sequences, were isolated (see Table 1).

Single wells of a flatbottom 96 well high binding E.I.A./R.I.A. plate (Costar) were coated overnight with 10 µg streptavidin (Pierce) in 100 µl 100 mM $NaHCO_3$ at 4° C. After a single wash with water, wells were incubated with 100 µl (10.7 µg) of biotinylated (D)-SH3 for 1 hr. at 20° C., blocked for 2 hrs with 30 mg/ml dialyzed bovine serum albumin (BSA) in 100 mM $NaHCO_3$, and again incubated with 100 µl (10.7 µMg) of biotinylated (D)-SH3 for 1 hr. Unliganded streptavidin was blocked for 30 minutes by the addition of 8 µl 5 mM biotin in tris-buffered saline (TBS). Wells were subsequently washed 5 times with phosphate buffered saline (PBS) and 0.1% Tween-20, and incubated overnight with 50 µl of the phage stock in TBS/$NaN_3$ and 50 µl of TBS, 0.1% Tween-20, 1 mg/ml BSA and 0.05% $NaN_3$. Wells were subsequently washed by six additions of 200 µl of TBS, 0.1% Tween-20 and 1 mg/ml BSA with increasing incubation times in the later rounds of the selection procedure. (D)-SH3 bound phage particles were subsequently eluted by the addition of 100 µl D-SH3 ligand peptide (715 µM), sequence D-YGGRELPPLPRF-amide (SEQ ID No: 2), for 15 minutes at 4° C., at a final concentration of 700 to 1000 µM peptide. Acid elution of phages in this screen gives no detectable preferential binding to D-SH3 coated wells after four rounds of selection. The eluate was subsequently used to infect K91-kan cells. Briefly 100 µl eluate was mixed with 100 µl K91 Terrific Broth cells (prepared as described) an incubated for 20 minutes at room temperature. The mixture was subsequently transferred into an Erlenmeyer flask containing 20 ml LB/0.2 µg/ml tetracycline. After 1 hr incubation while shaking at 37° C., tetracycline was added to a final concentration of 20 µg/ml, appropriate dilutions were plated on tetracycline-containing plates (20g/ml) to determine the titer of the eluate and the culture was incubated at 37° C. for 12–16 hrs. Phage were isolated from the supernatant by two PEG precipitations and the resulting phage stock was used for titering to determine the yield, and for the subsequent round of selection. In the fourth round of selection, phage were incubated in wells coated with or without the D-SH3 domain to determine the specificity of the capture. The washing conditions and yields of the different rounds of selection were as follows:

| Round | Washing Conditions | Yield D-SH3 coated | Control |
|---|---|---|---|
| 1 | 6×, no incubation | $1:3 \times 10^5$ | n.a. |
| 2 | 6 × 3 minutes at 4° C. | $1:1 \times 10^6$ | n.a. |
| 3 | 6 × 5 minutes at 4° C. | $1:2 \times 10^4$ | n.a. |
| 4 | 6 × 10 minutes at 4° C. | $1:2 \times 10^4$ | $1:4 \times 10^5$ |

From these data it is apparent that 1) in subsequent rounds phage that bind more tightly are selected since the yield increases although the washing conditions get significantly harsher and 2) this binding is specific for the D-SH3 domain since elution is achieved by incubation with a substrate for this domain, and more importantly, since the recovery of phage particles in round 4 is 20-fold higher in the presence of the D-SH3 domain than in the absence (recovery is higher from the D-SH3 domain-coated plates). A larger number of phage particles was retained in the presence of the D-SH3 domain than in its absence.

When the (D)-SH3 domain was used to screen this library a series of peptides were isolated that were grouped in three classes. These peptides all interact with the substrate binding site of the SH3 domain as they were eluted with the (D)-YGGRELPPLPRF peptide (SEQ ID NO:2). Surprisingly, all peptides contained a pair of cysteine residues, a property that is not observed for the polyproline peptides that interact with the (L)-SH3 domain. The disulfide bond may increase the affinity of these peptides for the (D)-SH3 domain by reducing the total number of possible conformers. Peptides in groups I and III contained at least a single arginine residue that may form a salt bridge with aspartic acid99 in the SH3 domain and which interacts with arginine residues in Src-binding poly proline peptides (Feng, S., et al., *Science* 266:1241 (1994)).

TABLE 1

Sequences of phage-displayed peptides that interact with the (D)-Src SH3 domain.

| Sequence | Number of Isolates low stringency | high stringency | Type |
|---|---|---|---|
| Group I | | | |
| CKRFVWRGQALC (SEQ ID NO: 13) | 10 | 14 | |
| CSRASWRGLLFC (SEQ ID NO: 14) | | 1 | |
| Group II | | | |
| CWYLGYWPGQEC (SEQ ID NO: 15) | 12 | | |
| Group III | | | |
| CLSGLRLGLVPC (SEQ ID NO: 16) | 2 | | fdSCR-1 |
| CLMGLRLGLLPC | 4 | | fdSRC-1 |
| CAYGFKLGLIKC (SEQ ID NO: 18) | 1* | fdSRC-3 | |

*This phage clone has an alanine to arginine substitution directly amino terminal to the insert region.

Conserved residues between different members of the groups I and III are indicated in bold, semiconserved residues are underlined. Note that for all members of group I and III the positioning of the conserved residues relative to the cysteine residues is preserved. Individual phage clones representing inserts of all 3 groups were analyzed after four to five rounds of selection for binding to the (D)-Src SH3 domain. All clones bind at least 150 fold better to wells coated with 0.5 µg streptavidin and 1.3 µg of the Src SH3 domain than to control wells. In both the low stringency and the high stringency screen, individual colonies were analyzed after 4 rounds of selection. Both the high and low stringency screen were based on the same initial round of selection. Differences between the high stringency and low stringency screen include a 2 fold decrease in the concentration of (D)-Src SH3 used to coat the wells, a decrease in the incubation time of the phage on the plate (from 16 hrs. to 1 hr.), and an increase in the incubation time between the six washes of the plate (low stringency screen: round 2,3 and 4,3', 5' and 10' resp.; high stringency screen: rounds 2 to 4 all 10' incubations).

Phage display with the L-SH3 domain was also assessed. When the (L)-SH3 domain is used to screen a phage library (A12) for interacting sequences the poly-proline sequences that have been observed by others Rickles, R. J., et al., *EMBO J.*, 13:5598 (1994); Sparks, A. B., *J. Biol. Chem.*, 39:23853 (1994); Cheadle, C., et al., *Ibid*, 39:24034 (1994) are isolated. The results are as follows and showed that the display worked:

Bait
After 4 rounds
L P E V P P L V A P (SEQ ID No: 7)
L A R S R L P A I P (SEQ ID NO: 8)
R M S P L V P L R N (SEQ ID No: 9)
GCN4 leucine zipper: short (33 residues), but low probability
c-Src SH-3 domain: 60 residues, bind peptides (type II polyPro)
GCN4 leucine zipper: synthesis straightforward, CD as expected after 5 rounds no difference in recovery +/− zipper Test 59 individual clones, no difference +/− zipper
Src SH3 domain: Src (L-) SH3 binds to substrate in a stereo-specific manner Src (L-) SH3 selects poly-Pro sequences from library:

Sequence analysis of a small number of isolates after four rounds of selection with the L-SH3 domain revealed the following two peptide sequences: CLARSRLPAIPS (SEQ ID NO: 10) (nine isolates) and SRMSPLVPLRNS (SEQ ID NO: 21) (one isolate). The sequences of these peptides have features consistent with those described for class I and class II ligands of the SH3 domain ((Yu, H., et al., *Cell*, 76:933 (1994); Rickles, R. J. et al., *EMBO J.*, 13:5598 (1994; Sparks, A. B., et al., *J. Biol. Chem.*, 269:23853 (1994); Cheadle, C., et al., *ibid.*, p. 24034)).

Analysis of single phage clones

To analyze the specificity of this interaction more rigorously, 6 individual colonies obtained after 4 rounds of selection were grown up in LB/20 µg/ml tetracycline. Phage particles were isolated from 1.3 ml supernatant by PEG precipitation and were resuspended in 500 5 µl TBS giving an estimated concentration of $6.5 \times 10^{10}$ transforming units/ml. 0.2 µl aliquots (approximately $1.3 \times 10^7$ TU) were incubated in 50 µl TBS/0.1% Tween 20/1 mg/ml BSA in wells that had been coated as described above but with 0.5 rather than 10 µg streptavidin and with or without 1.3 µg D-SH3. After the incubation with phage non-bound phage were removed by 6(3 minute), washes with 150 µl TBS/0.1% Tween20/1 mg/ml BSA. Bound phage particles were subsequently eluted with 40 µl glycinecine HCl pH2.2/1 mg/ml BSA for 10 minutes at 4° C. The eluate was subsequently brought to neutral pH and titered on K91 kan cells as described above.

| Clone | Recover (arbitrary units)* D-SH3 coated | control | Ratio D-SH3/control |
|---|---|---|---|
| 1 | 1664 | 5 | 333 |
| 2 | 1840 | 1 | 1840 |
| 3 | 1316 | 0 | >1316 |
| 4 | 2348 | 0 | >2348 |
| 5 | 1472 | 3 | 491 |
| 6 | 1348 | 9 | 150 |

*Calculated from the number of colonies/plate at a given dilution.

Individual clones were analyzed after four and five rounds of selection. In subsequent rounds, the incubation time between washes was increased (times of 0, 3, 5, 10 and 10 rain, respectively, for rounds 1 through 5). After four rounds of selection, 29 clones were sequenced, of which only 7 are within Group III of Table 1. To ensure that the selected phages were not binding to streptavidin or to a composite surface formed by the streptavidin- D-SH3 complex, a fifth selection round was performed with neutravidin (Pierce) as a matrix. Sequence analysis of clones after this fifth round of selection revealed only sequences of the fdSRC-2-type. Preliminary experiments suggest that the affinity of the corresponding peptide, Pep-D2, is similar to that of Pep-D1. Pep-D1 corresponds to the fdSRC-1 insert CLSGLRLGLVPC (SEQ ID No: 16) (Table 1), with the COOH-terminal alanine that is present in all flanking sequences (see Example 2). The other phage isolates obtained after four rounds of selection expressed one of the following two sequences: CKRFVWRGQALC (SEQ ID No: 13) (10 isolates) and CWYLGYWPGQEC (SEQ ID No: 15) (12 isolates). The first of these sequences resembles the background sequences that are isolated with a variety of biotinylated ligates (Smith, G. P. and Scott, J. K., *Methods in Enzymol.*, 217:228 (1993)) and is also similar to a sequence that was isolated previously with a monoclonal antibody against myohemerythrin, although it does not conform to the recognition motif for this antibody (Smith, G. P. and Scott, J. K., *Science*, 249:386 (1990)). This sequence is therefore likely to bind to some component in the system other than the SH3 domain. Indeed, a D-amino acid version of this sequence fails to bind to the L-SH3 domain, as judged by ELISA and NMR studies. The other sequence that was picked up after four rounds of selection shows limited similarity to the first sequence and has not been examined further.

EXAMPLE 2

An All D Amino Acid Src SH3 Domain Binds to the L Src SH3 Domain

The (D)-amino acid peptide denoted Pep-D1, (D)-RCLSGLRLGLVPCA (SEQ ID NO:11, a representative sequence of group III sequences), which is the mirror image of one of the phage-displayed peptides that binds to the D-Src SH3 domain, was synthesized and its interaction with the bacterially expressed (L)-SH3 domain was examined. Pep-D1 corresponds to the fdSRC-1 insert CLSGLRLGLVPC (SEQ ID No: 16) (Table 1), with the COOH-terminal alanine that is present in all flanking sequences. The arginine immediately preceding the first cysteine residue was observed in the fdSRC-3 sequence (Table 1). The presence of arginine and lysine residues close to the $NH_2$-terminus of secretory and transmembrane proteins negatively affects protein translocation (Boyd, D. and Beckwith, J., *Cell*, 62:1031 (1990)). In addition, a selection against arginine residues in the $NH_2$-terminal part of phage pIII fusions has been observed (Cunningham, B. C. et al., *EMBO J.*, 13:2508 (1994)). The alanine to arginine mutation in this clone may thus increase the affinity of the insert sequence for the D-SH3 domain, and could improve the solubility of the peptide; it was therefore included in the synthetic peptide. For affinity measures, an $NH_2$ terminal D-tyrosine was added to the peptide for concentration determination (Edelhoch, H., *Biochemistry*, 6:1948 (1967). The peptides with and without the $NH_2$ terminal tyrosine were air-oxidized in 100 mM tris, pH 8.5, for 48 hours at a concentration of 1 mg/ml. Oxidized peptide was purified by reverse-phase HPLC with a $C_{18}$ column and a water-acetonitrile gradient in 0.1% trifluoroacetic acid. The identify of the products was confirmed by laser desorption mass spectrometry.

The reduced form of Pep-D1 shows no detectable binding activity in this assay ($K_d$>>800 μM), which indicates that the formation of the disulfide is required for efficient binding. The affinity of Pep-DI for the L-SH3 domain was determined by a competitive enzyme-linked immunosorbent assay (ELISA). Single wells of a 96-well plate were coated with 5 μg of the L-SH3 domain (Scott, J. K. and Smith, G. P., *Science*, 249:386 (1990); Smith, G. P. and Scott, J. K., *Methods in Enzymol.*, 217:228 (1993)). Wells were blocked with BSA, and phages expressing the L-SH3-binding insert CLARSRLPAIPS (SEQ ID NO: 10) were allowed to bind in 10 mM $NaHPO_4$, pH 7.2, 15 mM NaCl, 1 mg/ml of BSA, 0.05% $NaN_3$, and 0.1% Tween 20, in the presence of increasing amounts of competitor peptide. Phage binding was quantified with a rabbit M13 antibody (Stratagene) and alkaline phosphatase-labeled goat antibody to rabbit (Pierce), with a fresh solution of p-nitrophenol phosphate as substrate. Absorbance at 410 nm was determined with a Dynatech micotiter plate reader. Titration curves (means of triplicates) were obtained for the L-peptide ligand YGGRELPPLPRF amide (SEQ ID NO: 2) and the D-peptide ligand Pep-D1 YRCLSGLRLGLVPCA (SEQ ID NO: 22) in the presence and absence of 25 mM dithiothreitol. Relative values for $K_d$ were obtained as described (Minor, D. L., Jr. and Kim, P. S., *Nature*, 367:660 (1994)). The $K_d$ of the L-peptide YGGRELPPLPRF-amide (SEQ ID NO: 2) was determined to be 6.0 μM by direct tryptophan fluorescence spectroscopy. A solution of the peptide was titrated into 1 μM SH3 solution in 15 mM NaCl and 10 mM $NaHPO_4$, pH 7.2. Tryptophan fluorescence was induced by excitation at 295 nm (5 nm slit width), and emission was measured at 339 nm (10 nm slit width), with a Hitachi F-4500 fluorescence spectrometer. The dissociation constant was determined by Scatchard analysis.

Although the syntheses of the (D)-enantiomeric form of both rubredoxin (45 amino acids) and human immunodeficiency virus (HIV) protease (99 amino acids) have been described Del Milton, R. C., et al., *Science*, 256:1445 (1992); Petsko, G. A., *Ibid*, 256:1403 (1992); Zawadzke, L. E. and Berg, J. M., *J. Am. Chem. Soc.*, 114:4002 (1992); Zawadzke, L. E. and Berg, J. M., *Proteins*, 16:301 (1993)), for most proteins the synthesis of the full (D)-enantiomeric form will not be feasible because of size limitations on the likelihood of successful chemical synthesis. However, both intracellular and extracellular proteins are often composed of autonomous domains of 100 amino acids or less (reviewed in Bork, P. and Bairoch, A., *Trends Biochem. Sci.*, 20, poster (1995) for extracellular proteins; Doolittle, R. F., and Bork, P., *Sci. Am.*, 269:50 (1993); Efimov, A. V., *FEBS Lett.*, 355:213 (1994); Cohen, G. B., et al., *Cell*, 80:237 (1995)). This size range is within reach of current solid-phase peptide synthesis technology, and recent advances in chemical ligation strategies for unprotected protein fragments hold promise for the synthesis of even larger protein domains. Thus, the isolation of ligands for proteins of interest (e.g., multidomain proteins) may be achieved through the synthesis and screening of one of its constituent domains, as described here for the SH3 domain.

EXAMPLE 3

Determination of the Binding Site of the D-Peptide in the SH3 Domain

Heteronuclear magnetic resonance (NMR) experiments were performed on the $^{15}$N-labeled SH3 domain in the absence and presence of Pep-D1 to determine the binding site of this D-peptide in the SH3 domain. Residues in the SH3 domain that interact with Pep-D1 were identified through changes in amide $^1$H or $^{15}$N chemical shifts upon the addition of the D-peptide ligand.

The ligand-binding site of the SH3 domain for its natural, L-amino acid ligands consists of three pockets that together form a relatively shallow groove on one side of the molecule (Feng, S., et al., *Science*, 266:1241 (1994); Yu, H., et al., *Science*, 258:1665 (1992)). Pocket A, which is formed by the side chains of aspartic acid[99] and tryptophan[118], accommodates the conserved arginine residue, whereas pockets B and C form a hydrophobic surface that accommodates the aliphatic and proline residues in SH3 ligands (Feng, S. et al., *Science*, 266:1241 (1994); Yu, H. et al., *Science*, 258:1665 (1992)).

Uniformly ($\geq$ 95%) $^{15}$N-labeled SH3 domains were obtained by growing *E. coli* harboring the plasmid pMMHb-SRC SH3 in M9 medium supplemented with ($^{15}$NH$_4$)$_2$SO$_4$ (99.7% $^{15}$N; Isotec, Miamisburg, Ohio). Upon reaching an absorbance of 0.6 at 600 nm, cells were induced for 4 hours with 0.4 mM IPTG. The protein was purified as described for the unlabeled material. Spectra were collected on a Bruker AMX 500 MHz NMR spectrometer. Resonance assignments were made by standard methods (Wuthrich, K., *NMR of Proteins and Nucleic Acids* (Wiley, N.Y., 1986); McIntosh, L. P. et al., *Biochemistry*, 29:6341 (1990)) and were consistent with the assignments for SH3 (Yu, H. et al., *FEBS LETT.*, 324:87 (1993)). The peptide Pep-D1 was added to solution containing the $^{15}$N-labeled SH3 domain to a ratio of 1.5:1 (peptide:protein) in 10 mM phosphate, pH 6.0, at 298 K; heteronuclear single quantum coherence (HSQC) spectra (Bodenhausen, G. and Rubin, D. J., *Chem. Phys. Lett.*, 69:185 (1980) of the uncomplexed and complexed forms were compared. There were no resonances with chemical shift differences >0.04 p.p.m. i the $^1$H dimension, or >0.17 p.p.m. in the $^{15}$N dimension. However, a number of resonances were reduced in intensity or completely absent in HSQC spectra of the complex. Residues that had the intensity of their HSQC resonances reduced significantly upon Pep-D1 binding, as compared to the ligand-free spectra, were identified as follows: for individual peaks, the ratio of peak intensities in the absence and presence of peptide was determined and converted to a log scale. The resulting distribution around the median is markedly skewed toward the left. A window that included >90% of the residues with ratios that were higher than the median was applied to residues with chemical shifts below the median. Only residues with a ratio lower than the median and that were not contained within this window were considered to have undergone significant perturbation (according to these criteria, only residues with a ratio that was reduced to less than 0.65 of that of the median were considered to have undergone significant perturbation). These residues include residues 94, 97, 112, 115, 117, 119, 120, 131, 132 and 135, the indole resonance of tryptophan[119], and the side chain amides of asparagine[113], and asparagine[135]. The resonances of 95, 96, 98, 99, 100, 118 and 134 and the indole resonance of tryptophan11g were absent in the presence of ligand. Control experiments, using the L-peptide YGGRELPPLPRF amide (SEQ ID NO: 2) resulted in 17 resonances that were shifted by $\geq$ $^3$0.1 p.p.m. in the $^1$H dimension or $\geq$ $^3$0.5 p.p.m. in the $^{15}$N dimension (residues 87, 89, 90, 92, 96, 98, 99, 100, 109, 111, 114, 116, 119, 121, 131, 132 and 135, the indole resonance of tryptophan[119], and the side chain amides of asparagine[113] and asparagine[135]). Five resonances (95, 97, 117, 118 and 134) were absent in HSQC spectra of the complex. To validate the approach chosen to identify residues that interact with Pep-D1, this approach was applied to the spectra obtained with the peptide L-YGGRELPPLPRF amide (SEQ ID NO: 2). With this approach, no new residues were identified that interacted with this peptide. The effect of peptide binding on the chemical shift of proline[133]$_1$ which forms part of pocket B, could not be observed in this type of experiment.

The binding of Pep-Di results in the perturbation of the chemical shifts of the residues that form pocket A, as well as a patch of adjacent residues (FIG. 2C). Most of these residues also undergo changes in their chemical shifts upon binding of the L-peptide (FIG. 2B). Pocket A is likely to interact with the conserved arginine or lysine residues in the D-peptides in a manner that is analogous to the recognition of arginine residues in L-amino acid ligands. The interaction of this site with both the L- and D-amino acid ligands explains the competition observed for the binding of these two ligands.

Pep-D1 appears to occupy only part of the binding site that is contacted by the polyproline-type ligands for the SH3 domain (FIG. 3). Residues that form part of pocket B and pocket C (tyrosine[90] and tyrosine[92]), or that are adjacent to this pocket (valine[87] and leucine[89]), are not perturbed upon binding of Pep-D1 (FIGS. 2 and 3). Mutational analysis suggests that, for L-amino acid ligands, interactions at these sites are required for highaffinity binding (Feng, S. et al., *Science*, 266:1241 (1994). D-peptide inhibitors of higher affinity could therefore potentially be obtained by the design or selection of analogs of Pep-D1 or Pep-D2 (Table 1) that extend further along the groove, into pocket C of the SH3 domain.

EXAMPLE 4

Use of the D-amino acid peptide ligands to design highly-enriched libraries

Random synthetic libraries do not cover enough conformational space to always allow for the isolation of high affinity ligands for a given target. A more promising strategy is the use of libraries that are biased towards structural elements known to interact with a target of interest. Specifically, the D-amino acid peptide sequences that interact with a given target that are isolated using the strategy described here are used as guidelines for the design of biased (D)-amino acid peptide and peptide-based libraries. These biased libraries may subsequently be used for the isolation of novel ligands. For example, the three classes of (D)-amino acid peptide ligands for the SH3 domain (Example 2) are useful to design (D)-amino acid peptide-based libraries highly enriched for SH3-binding peptides or peptidomimetics. Such libraries are useful to identify peptides which bind the SH3 domain and are particularly useful because they are biased toward (have an enhanced content of) peptides known to bind the SH3 domain. All SH3 domains for which the interaction with (L)-amino acid peptides has been examined bind to ligands with similar structural elements. Synthetic libraries based on the structure of (D)-amino acid ligands for the SH3 domain are also enriched in ligands for other SH3 domains. The biased libraries based on the structure of the (D)-amino acid peptide ligands for the SH3 domain are useful for the isolation of ligands for a variety of SH3 domains.

A biased library is constructed, for example, as follows, based on the amino acid sequences of the 3 classes of peptides described in Example 2, which have been shown to bind the (D)-SH3 domain. A chemical peptide library of D-amino acids is prepared in which about 80% of the D-amino acid peptides of the library have the conserved amino acid residues and about 20% of the D-amino acid peptides of the library do not have the conserved amino acid residues.

Thus, the library, which is heavily biased for peptides having the general structure of peptides known to bind (D)-SH3 domain (i.e., 80%), can be used to isolate other D-amino acid peptides which have the conserved structure and bind to other SH3 domains (i.e., human). In addition, D-amino acid peptides in which the conserved amino acid residue has been altered (i.e., from the 20% of the D-amino acid peptides) and which binds to the SH3 domain with equivalent or greater affinity, can be isolated.

EXAMPLE 5

Mirror Image Selection of an Enantiomeric DNA Inhibitor of Vasopressin

Vasopressin was prepared using conventional solid phase peptide synthesis.

In the first step toward generating an antagonist of the peptide hormone L-vasopressin, an in vitro selection was used to isolate single-stranded DNAs (ssDNAs) that bind synthetic D-vasopressin (DVP). A starting pool of $10^{16}$ different 96-mers was synthesized on a DNA synthesizer. Each pool molecule contained a central region with 60 random-sequence positions that was flanked by two 18-nt defined regions. Molecules within this starting pool that bind DVP were enriched by affinity chromatography. The affinity resin was prepared by coupling biotinylated DVP to streptavidin agarose. The ssDNA pool was radiolabeled, denatured, renatured in a physiological buffer and passed over this resin. After extensively washing the column, molecules that bind DVP were eluted from the column with a molar excess of DVP. Eluted pool was amplified by PCR using a negative-strand "primer-terminator", that is, an oligonucleotide bearing a central segment of non-nucleotide material that blocks further extension of the positive strand (Williams, K. P. and Bartel, D. P., Nucleic Acids Res., 23:4220–4221 (1995)). Such PCR results in a substantial size difference between the two product strands, facilitating gel-purification of the positivestrand ssDNA pool. This combination of affinity chromatography and PCR constituted one cycle of selection amplification.

After thirteen iterations of the selectionamplification cycle the pool was cloned. Analysis of 56 clones revealed only two different sequences, 96.2 and 96.4. Positive ssDNA of each sequence binds DVP and both have potential to form very similar secondary structures. Affinity chromatography studies of a set of deletion mutants has identified one, 69.1, that appears to bind DVP better than does the parent sequence. This aptamer is not eluted from the DVP resin by L-vasopressin.

96.2
TCTAACGTGAATGATAGAcggcgaatc-
cccaatgcgaagcagtggttttgca
GTCGAGTTGCTGTGTGCCGATGAgcgT-
TAACTTATTCGACCAAA (SEQ ID NO:23)

96.4
TCTAACGTGAATGATAGAcgttacgt-
gtctacactatGTCGAGTTGCTGT
GTGCCGATGAacgtgggattagagcgt-
gTTAACTTATTCGACCAAA (SEQ ID NO:24)

69.1
TCTAACGTGAATGATAGAcgttacgt-
gtctacactatGTCGAGTTGCTGT
GTGCCGATGAacgtgggat (SEQ ID NO:25)

D-vasopressin aptamers. Sequence blocks shared by the two original aptamers are in capital letters. The definedsequence segments that flanked the random-sequence region are indicated in bold. A segment derived from randomsequence positions that is shared by the two sequences of the final pool is in outline. The 69.1 aptamer is a deletion derivative of 96.4.

The information required to complete the selection-reflection procedures is described above. The synthesis of the 69.1 sequence using enantio-deoxyribose phosphoramidites will yield an aptamer that binds natural vasopressin but is not susceptible to nuclease degradation. However, before synthesizing such an aptamer, a second selection experiment can be performed, starting with a degenerate set of sequences based on the 69.1 sequence. This allows for isolation of sequence variants that bind DVP with higher affinity. Data from this second selection will also provide a reliable secondary structure model that will guide further deletion experiments, yielding a final DVP aptamer of smaller size and greater activity. This nuclease-proof aptamer will be tested in vitro as a ligand and in vivo as an antagonist of vasopressin.

Equivalents

Those skilled in the art will recognize, or be able to ascertain using no more than routine experimentation, many equivalents to the specific embodiments of the invention described herein. Such equivalents are intended to be encompassed by the following claims.

---

What is claimed is:

1. A method of producing a macromolecule of non-natural handedness that binds to a target macromolecule of natural handedness, comprising the steps of:
   a) providing an enantiomer of the target macromolecule;
   b) providing a library of macromolecules of natural handedness;
   c) contacting the library of b) with the enantiomer of a), under conditions appropriate for binding of a macromolecule of natural handedness in the library with the enantiomer of a), whereby the enantiomer of a) binds a macromolecule of natural handedness present in the library;
   d) producing the enantiomer of the macromolecule of natural handedness which is bound to the enantiomer of a), wherein the enantiomer of d) is a macromolecule of non-natural handedness which binds to the target macromolecule of natural handedness.

2. A method of producing a macromolecule of non-natural handedness that binds to a target macromolecule of natural handedness, comprising the steps of:
   a) providing an enantiomer of the target macromolecule;
   b) providing a library of macromolecules of natural handedness;
   c) contacting the library of b) with the enantiomer of a), under conditions appropriate for binding of a macromolecule of natural handedness in the library with the enantiomer of a); whereby the enantiomer of a) binds a macromolecule of natural handedness present in the library;
   d) identifying a macromolecule which is bound to the enantiomer of a);
   e) determining the sequence of the macromolecule of natural handedness identified in d); and
   f) producing a macromolecule of non-natural handedness which is the enantiomer of the macromolecule identified in d) or of a characteristic domain thereof, wherein the enantiomer of e) is a macromolecule of non-natural handedness which binds to the target macromolecule of natural handedness.

3. The method of claim 2 wherein the target macromolecule is a protein.

4. The method of claim 3 wherein the protein is selected from the group consisting of: vasopressin, interleukin-8, Thrombomodulin EGF-like domain, $GPII_b$-$III_a$ cytoplasmic domain, Factor VIIa GLA domain, Factor IX EGF-like domain, HIV protease, $NH_2$-terminal SH3 domain GRB2, COOH-terminal SH3 domain GRB2, P120$^{GAP}$ SH3 domain, vascular permeability factor and vascular endothelial growth factor.

5. The method of claim 2 wherein the target macromolecule is an oligonucleotide.

6. The method of claim 5 wherein the oligonucleotide is selected from the group consisting of: HIV RRE, HIV Tar and BCR-AB1 fusion DNA sequences.

7. A method of producing a D amino acid peptide that binds to a target L macromolecule, comprising the steps of:
   a) providing a D amino acid peptide of the target L macromolecule;
   b) providing a library of L amino acid peptides;
   c) contacting the library of b) with the D amino acid peptide of a), under conditions appropriate for binding of an L amino acid peptide in the library with the D amino acid peptide of a) whereby the peptide of a) binds an L amino acid peptide present in the library;
   d) identifying an L amino acid peptide which is bound to the D amino acid peptide of a);
   e) determining the sequence of the L amino acid peptide identified in d); and
   f) producing a D amino acid peptide of the L amino acid peptide identified in d) or of a characteristic domain thereof, wherein the D amino acid peptide of e) binds to the target L macromolecule.

8. The method of claim 7 wherein the peptide is selected from the group consisting of: vasopressin, interleukin-8, Thrombomodulin EGF-like domain, $GPII_b$-$III_a$ cytoplasmic domain, Factor VIIa GLA domain, Factor IX EGF-like domain, HIV protease, $NH_2$-terminal SH3 domain GRB2, COOH-terminal SH3 domain GRB2, P120$^{GAP}$ SH3 domain, vascular permeability factor and vascular endothelial growth factor.

9. A method of producing an L oligonucleotide that binds to a target L macromolecule, comprising the steps of:
   a) providing a D amino acid peptide of the target L macromolecule;

b) providing a library of D oligonucleotide;

c) contacting the library of b) with the D amino acid peptide of a), under conditions appropriate for binding of a D oligonucleotide in the library with the D amino acid peptide of a), whereby the peptide of a) binds a D oligonucleotide present in the library;

d) identifying a D oligonucleotide which is bound to the D amino acid peptide of a);

e) determining the sequence of the D oligonucleotide identified in d); and f) producing an L oligonucleotide of the D oligonucleotide identified in d) or of a characteristic domain thereof, wherein the L oligonucleotide of e) binds to the target L macromolecule.

10. The method of claim 9 wherein the macromolecule is selected from the group consisting of: vasopressin, interleukin-8, Thrombomodulin EGF-like domain, $GPII_b$-$III_a$ cytoplasmic domain, Factor VIIa GLA domain, Factor IX EGF-like domain, HIV protease, $NH_2$-terminal SH3 domain GRB2, COOH-terminal SH3 domain GRB2, $P120^{GAP}$ SH3 domain, vascular permeability factor and vascular endothelial growth factor.

11. A method of identifying an L amino acid peptide which binds a D amino acid peptide of interest, comprising the steps of:

a) providing a phage display library which comprises L amino acid peptides displayed on phage surfaces;

b) contacting the phage display library of a) with the D amino acid peptide of interest, under conditions appropriate for binding of L amino acid peptides displayed on phage surfaces with the D amino acid peptide of interest; and c) identifying phages on the surfaces of which the D amino acid peptide of interest is bound to an L amino acid peptide displayed on the surface, thereby producing a D amino acid peptide-displayed L amino acid peptide complex wherein the displayed L amino acid peptide is an L amino acid peptide which binds the D amino acid of interest.

12. The method of claim 11 further comprising making a D amino acid peptide which corresponds to the L amino acid identified and further comprising the steps of:

d) determining the amino acid sequence of the L amino acid peptide displayed on the surface of the phage; and e) synthesizing the D amino acid peptide which corresponds to the amino acid sequence of the L amino acid peptide determined in d), thereby producing a D amino acid peptide which corresponds the L amino acid peptide displayed on the surface.

13. The method of claim 11 wherein the L amino acid peptides displayed on the phage surfaces bind D amino acid peptides of the src SH3 domain.

14. A method of obtaining an L nucleic acid sequence which binds an L amino acid peptide of interest, comprising the steps of:

a) providing a collection of D nucleic acid sequences;

b) contacting the D nucleic acid sequences of a) with a D amino acid peptide of interest, under conditions appropriate for binding of the D nucleic acid sequences with the D amino acid peptide of interest;

c) isolate a D nucleic acid sequence which binds to the D amino acid peptide;

d) determine the nucleotide sequence of the D nucleic acid sequence of c); and e) prepare a nucleic acid sequence having the nucleotide sequence of d) using L nucleotides, wherein the nucleic acid sequence of e) is an L nucleic acid sequence which binds an L amino acid peptide.

* * * * *